United States Patent [19]

Kayser

[11] Patent Number: 5,419,768
[45] Date of Patent: May 30, 1995

[54] ELECTRICAL MEDICAL VACUUM REGULATOR

[75] Inventor: John P. Kayser, Madison, Wis.

[73] Assignee: Aeros Instruments, Inc., Gurnee, Ill.

[21] Appl. No.: 665,973

[22] Filed: Mar. 7, 1991

[51] Int. Cl.⁶ .............................................. A61M 1/00
[52] U.S. Cl. ................................ 604/119; 128/205.19; 128/205.24
[58] Field of Search .............. 128/205.19, 911, 28, 128/30, 30.2, 205.24; 137/487.5; 604/118, 119, 120, 50, 319

[56] References Cited

U.S. PATENT DOCUMENTS

| | | | |
|---|---|---|---|
| 1,620,322 | 3/1927 | Browne | 137/505.13 |
| 2,939,460 | 6/1960 | Sorensen | 604/120 |
| 3,086,528 | 4/1963 | Eichelman et al. | 604/120 |
| 3,599,639 | 8/1971 | Spotz | 604/119 |
| 3,675,653 | 7/1972 | Crowley et al. | 604/120 |
| 4,137,912 | 2/1979 | O'Neill | 128/204.29 |
| 4,213,457 | 7/1980 | Lewis | 604/120 |
| 4,238,991 | 12/1980 | Pickles | 92/85 A |
| 4,395,258 | 7/1983 | Wang et al. | 604/119 |
| 4,513,785 | 4/1985 | Kenny | 137/881 |
| 4,654,029 | 3/1987 | D'Antonio | 604/120 |
| 4,706,687 | 11/1987 | Rogers | 604/119 |
| 4,710,165 | 12/1987 | McNeil et al. | 604/50 |
| 4,718,895 | 1/1988 | Kurtz et al. | 604/119 |
| 4,795,428 | 1/1989 | Hwang | 604/118 |
| 4,795,448 | 1/1989 | Stacy et al. | 604/319 |
| 4,813,443 | 3/1989 | Pounder | 137/487.5 |
| 4,887,636 | 12/1989 | Rothen | 137/487.5 |
| 4,903,726 | 2/1990 | Martin et al. | 137/505.13 |
| 4,982,735 | 1/1991 | Yagata et al. | 128/30.2 |
| 4,988,336 | 1/1991 | Kohn | 604/119 |
| 5,101,808 | 4/1992 | Kobayashi et al. | 128/30.2 |
| 5,106,367 | 4/1992 | Ureche et al. | 604/119 |

Primary Examiner—Edgar S. Burr
Assistant Examiner—Aaron J. Lewis
Attorney, Agent, or Firm—Potthast & Ring

[57] ABSTRACT

A medical vacuum regulator (10) with a solenoid regulating valve (20) and a comparator (22) for electrically, automatically controlling the solenoid regulating valve (20) to intermittently open and close to achieve a preselected regulated vacuum (v) which is continuously provided or in intermittent mode decreases during a relaxation period (35) to atmosphere (30) and automatically increases during a ramp period (29) of a vacuum cycle (21) to prevent vacuum surge trauma to a patient (14). The regulating valve (20), in addition to regulating the vacuum during the vacuum cycle (21), continuously vents the system to atmosphere (30) when a patient venting solenoid valve (48) vents the patient (14) to atmosphere (30) to reduce the load on a vacuum pump (12). The continuous and intermittent modes of operation are selected by a mode selection circuit (36) with means for maintaining it in its selected state during a period of temporary power loss.

22 Claims, 5 Drawing Sheets

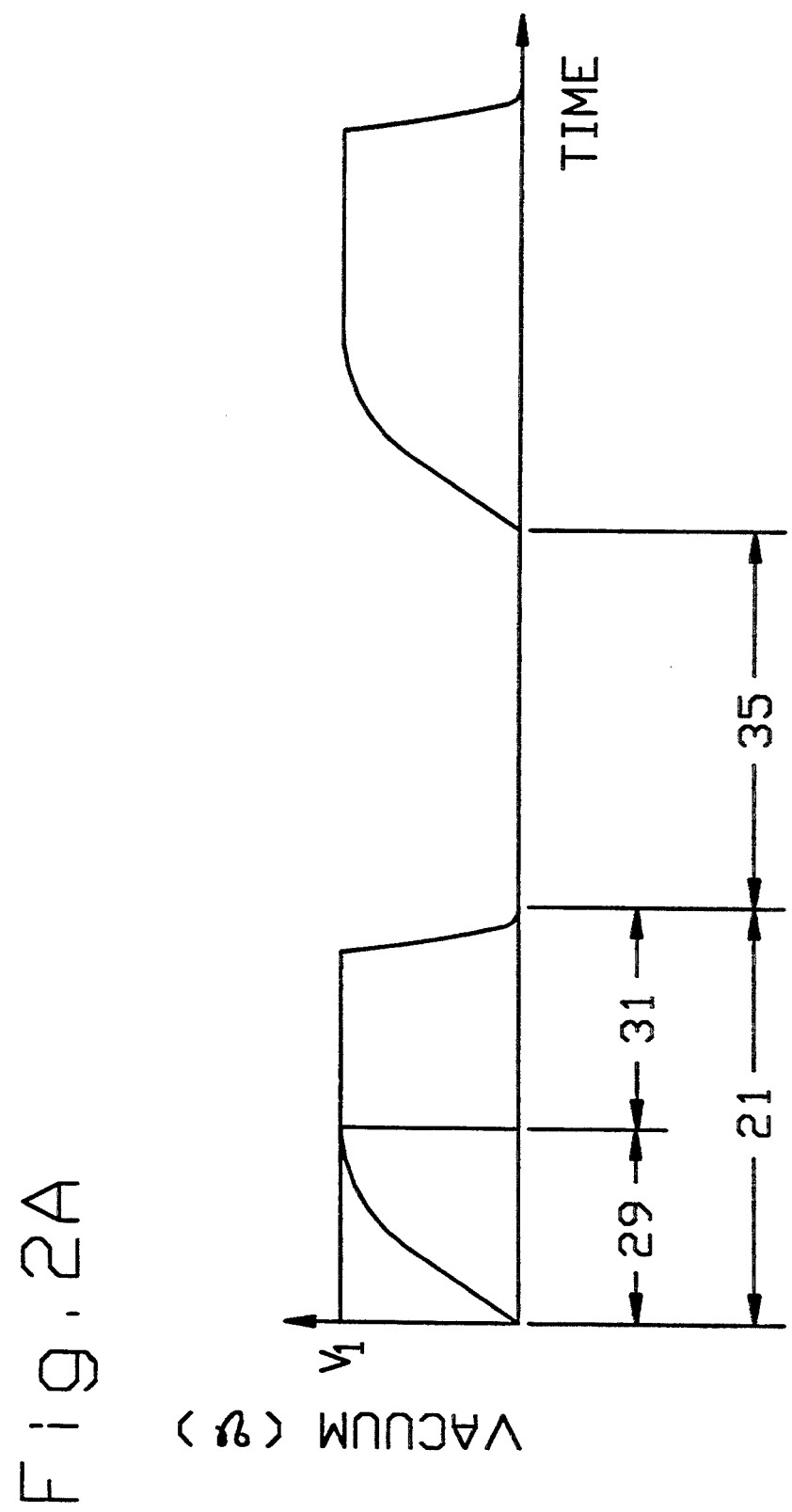

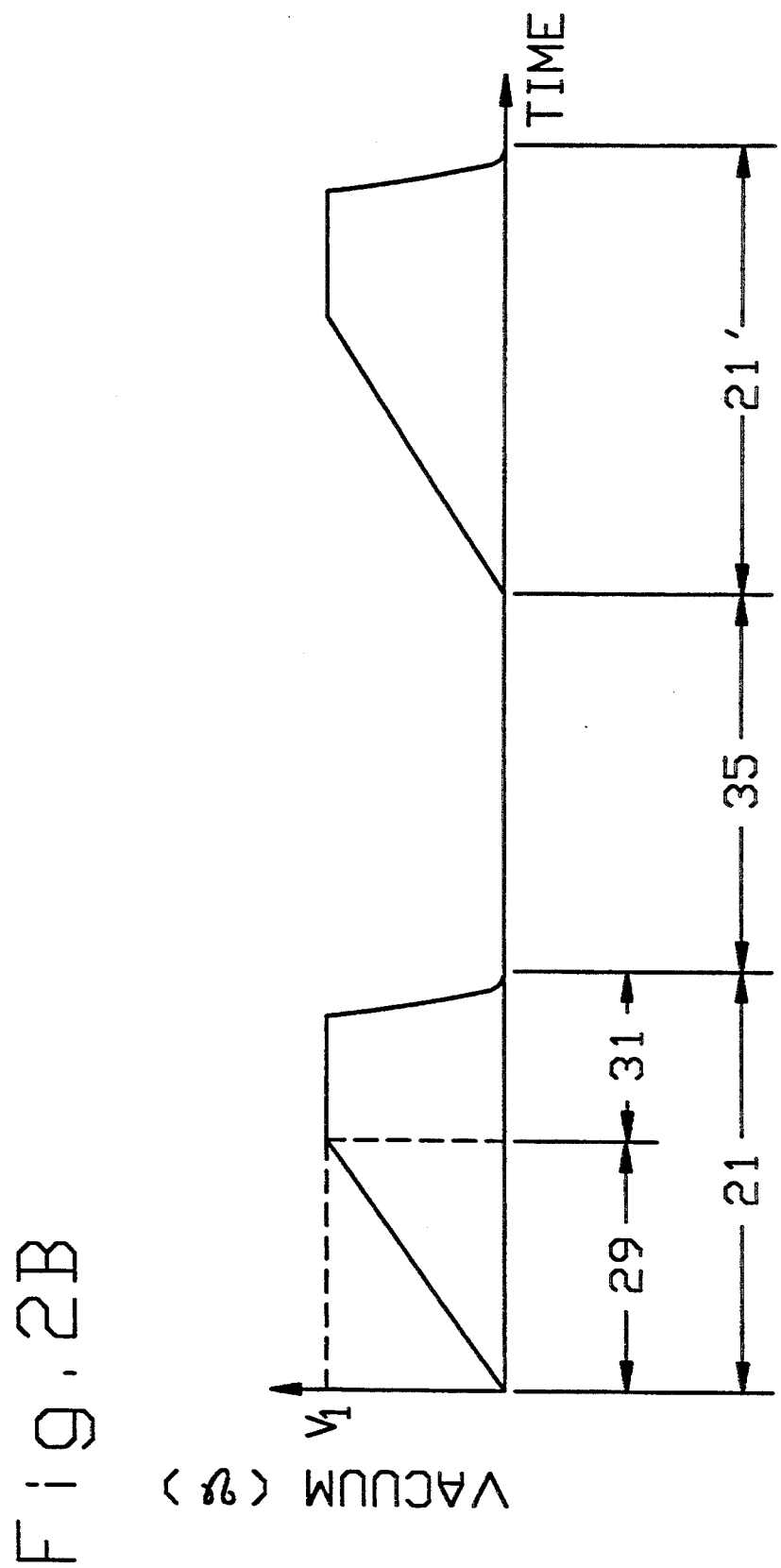

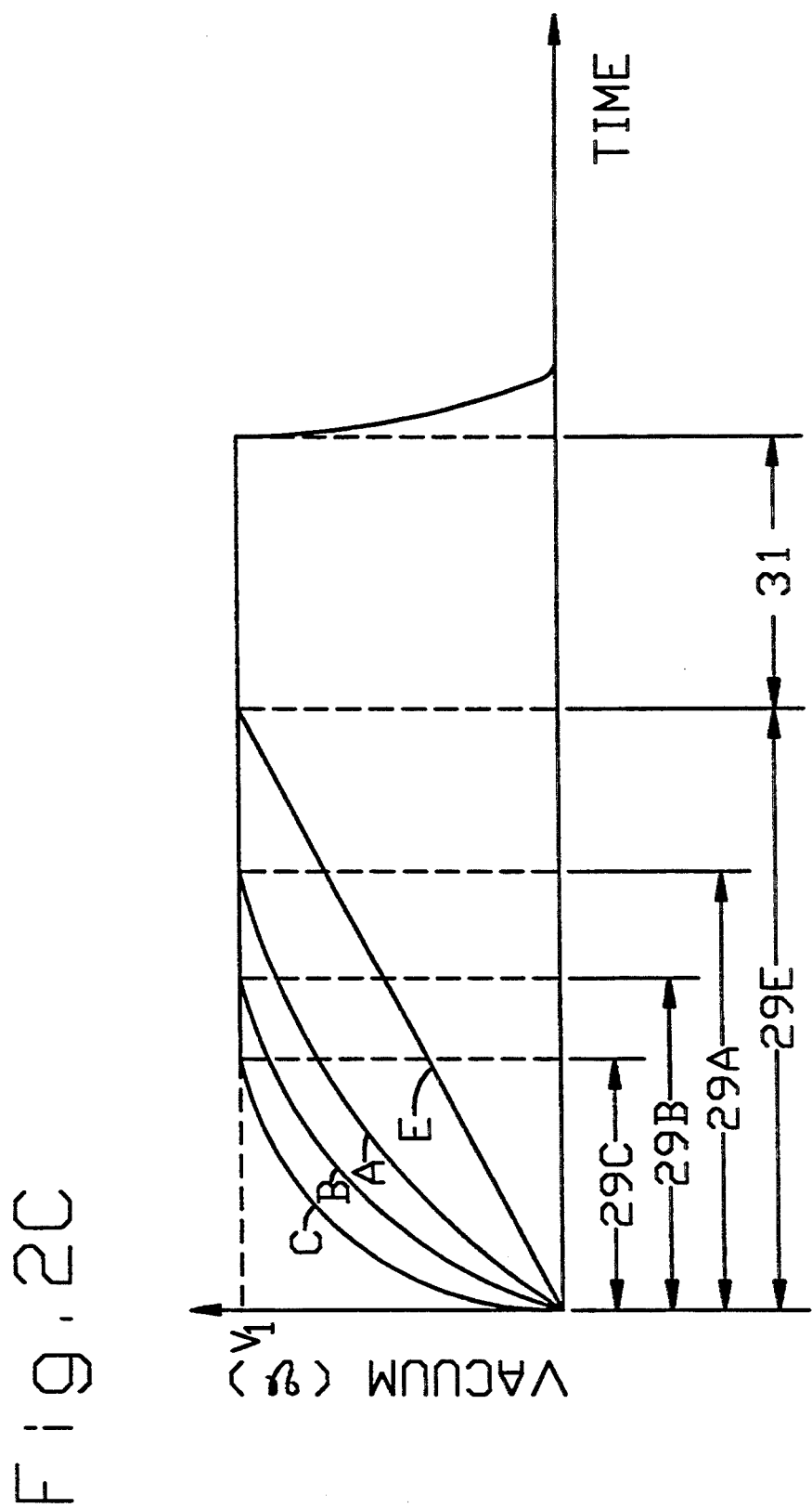

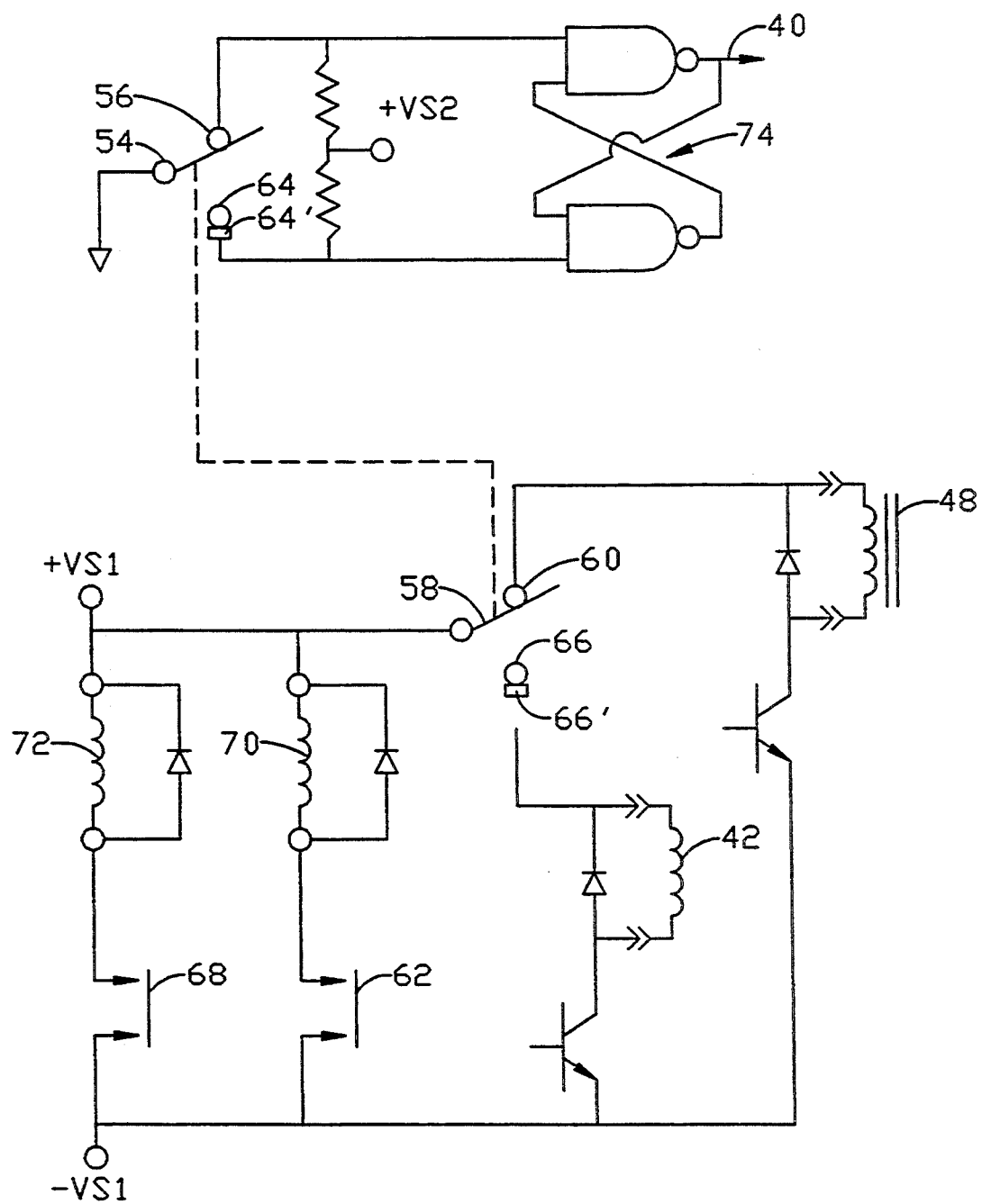

ELECTRICAL MEDICAL VACUUM REGULATOR

BACKGROUND OF THE INVENTION

This invention relates to a medical vacuum regulator and, more particularly, to an electrical medical vacuum regulator in which regulation control is by electrical means.

Medical vacuum regulators of the type which employ mechanical regulators are well known as illustrated by such a regulator shown in U.S. Pat. No. 4,903,726 of Martin et al. issued Feb. 27, 1990, and the other regulators shown in references cited therein. Generally, such mechanical regulators have pneumatic valves with mechanical feedback systems which enable them to control the opening and closing of the valve for respectively coupling and decoupling a patient vacuum delivery system, or patient, to a source of unregulated vacuum. Regulation of vacuum to the patient at a preselected vacuum level is thereby achieved mechanically. These mechanical regulators have been used in conjunction with solenoid on/off control valves to intermittently apply the regulated vacuum to the patient and, thus, to a degree are considered electrically controlled regulators. However, the actual vacuum regulation in these electrical regulators is achieved solely through mechanical means of well known construction. Thus, while it has been easy to intermittently connect and disconnect the regulated vacuum to the patient through means of electrical control, and to employ electrical displays of operation parameters, it has not been known how to regulate the actual level of vacuum except by manual manipulation of the pneumatic valves, themselves. This has caused electrical control of regulation levels on other than an on and off basis to be difficult if not practically impossible.

The patient delivery system generally includes an elongate plastic tube which is connected at one end to the outlet port of the regulator and at the opposite end to a sealed collection bottle. The sealed collection bottle, in turn, has an inlet connected to the patient through means of a flexible draw tube inserted into a body cavity of the patient, such as the stomach. The vacuum in the inlet tube causes body fluids to be drawn into the distal end of the draw tube in the body cavity, through the draw tube and into the collection bottle. It is common for the distal end of the draw tube within the body cavity to be adjacent or actually touching delicate tissues. Accordingly, a difficulty with this operation in known mechanically controlled regulators is that the initial surge of vacuum at the beginning of each time period of vacuum can move the distal end of the draw tube into the body cavity and thereby cause injury to the surrounding tissue. With continuous operation, the draw tube is more susceptible to blockage, but sometimes the additional strength of continuous vacuum is required. Thus, this operation continues to be employed despite the possible risk of injury to the patient, and such injuries continue to occur with known medical vacuum regulators.

Reliability is an important feature for medical vacuum regulators to possess, since the loss of vacuum source can be catastrophic for the patient. The vacuum pump motor is perhaps the most vulnerable element of the system. However, in known regulators, virtually no efforts have been made to maximize the useful life of the pump motor. In particular, in known medical vacuum regulators, the pump is forced to operate against a load which is inverse of the patients needs. If the patient needs low vacuum, the pump sees high vacuum. The pump is forced to operate against the maximum load when the patient is vented to atmosphere. This results in excessive wear on the vacuum pump motor and directly reduces reliability of the entire vacuum system of which the regulator is a part.

Another difficulty with known medical vacuum regulators which selectively operate in intermittent and continuous modes is that in the event of temporary power failure, unless mechanical switches are used that are unaffected by power failure, it is possible for the known regulators to come back to service when power is restored in a mode of operation which had not been prescribed for the patient. Such a result can be traumatic to the patient, but medical vacuum regulators with electronic mode selection switches are not provided with means for preventing such a result.

SUMMARY OF THE INVENTION

It is, therefore, an object of the present invention to provide a vacuum regulator in which the aforementioned problems and disadvantages are overcome, whereby the risk of injury to the patient is reduced while the degree of control of the applied regulated vacuum is enhanced. Generally, this objective is achieved by providing the vacuum regulator with an electrically controlled regulation valve which can be controlled to adjust vacuum levels according to selected changes in an electrical vacuum command signal. A regulator is provided having a regulating valve, means for preselecting a regulated vacuum level, and means responsive to the preselecting for generating signals to control the opening and closing of the regulating valve.

In accordance with the invention, by controlling a regulation valve, the vacuum applied to the patient is gradually increased at the beginning of each vacuum period during intermittent operation to reduce vacuum surge trauma to the patient. By venting the unregulated source to atmosphere during the relaxation periods of the intermittent operation cycle, the load on the vacuum pump is reduced, and its reliability is increased. Storing the selected operational mode during power failure, eliminates the risk to the patient of the regulator returning to operation in the incorrect mode.

More specifically, it is an objective to provide a vacuum regulator having a regulation chamber and means for connecting the regulation chamber to a source of unregulated vacuum with an improved controller, comprising a regulating valve connected with the regulation chamber and means for generating electrical signals for automatically controlling the regulating valve to intermittently open and close to achieve a preselected vacuum within the regulation chamber to reduce vacuum surge trauma. These signals are preferably electrical signals.

The objective of the invention is also achieved in part through provision of a controller in a medical vacuum regulator comprising means for regulating the level of vacuum applied to the patient and means for controlling the regulating means including means for intermittently decreasing, or relieving, the applied vacuum and means for automatically, intermittently, increasing the applied vacuum gradually.

The useful life of the vacuum pump motor is enhanced and another objective achieved by providing a controller for a medical vacuum regulator with means for venting the patient to atmosphere and means for automatically, continuously venting the source of vacuum to atmosphere. Thus, the source of vacuum is continuously vented to atmosphere whenever the patient's vacuum needs are less than the capability of the unregulated vacuum source. In the preferred embodiment, the regulation valve is also used to vent the unregulated source of vacuum during a relaxation period while regulating the vacuum level at other times.

Potential trauma to the patient is also reduced according to the invention by providing the medical vacuum regulator with a mode control circuit having means including an electronic mode selection switch manually actuatable for alternatively selecting a continuous mode and an intermittent mode, respectively, and means responsive to the electronic mode selection switch for selectively establishing operation in said continuous and intermittent modes including storing the last selection of the mode selection switch during a period of power loss.

Further, an objective of the invention is to provide a regulator with a regulator valve, means for preselecting a regulated vacuum level and means responsive to said preselecting means for generating signals to control opening and closing of the regulating valve.

BRIEF DESCRIPTION OF THE DRAWINGS

The foregoing objects, features and advantages will be described in greater detail and other objects and additional features are made apparent in the detailed description of the preferred embodiment which is given with reference to the several figures of the drawings, in which:

FIG. 2A is an illustrative waveform of the vacuum provided to the patient by a mechanical medical vacuum regulator of the prior art when operating in the intermittent mode;

FIG. 2B is an illustrative waveform of the vacuum provided to the patient by the medical vacuum regulator of FIG. 1 when operating in the intermittent mode;

FIG. 2C shows comparative waveforms of the variation of vacuum versus time for mechanical medical vacuum regulators of the prior art with various bottle volumes and for the medical vacuum regulator of FIG. 1; and FIG. 3 is a circuit schematic of a preferred implementation of the mode selection functional block of FIG. 1.

DETAILED DESCRIPTION

Figure 1:
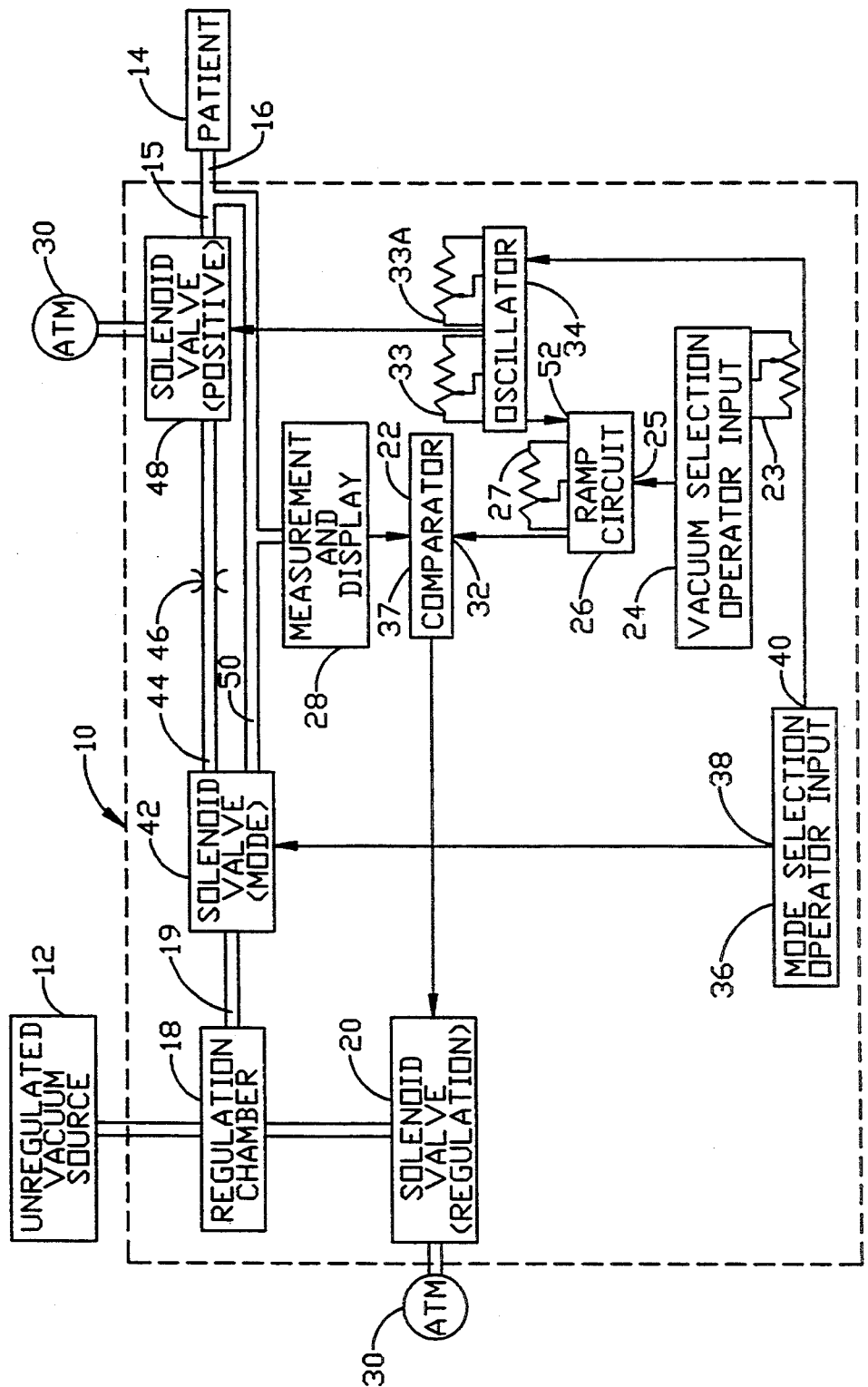
FIG. 1 is a functional block diagram of the medical vacuum regulator shown as connected between an unregulated vacuum source and a patient with pneumatic connections designated by double lines and electrical connections shown in a single line.

Referring now to the FIGS. 1 and 2B of the drawing, the preferred embodiment of the medical vacuum regulator 10 of the present invention is seen to operate between an unregulated vacuum source 12 and a patient 14. The connection to the patient 14 is through a patient delivery system 16 which typically includes an air tight collection bottle connected to an outlet 15 of the regulator 10 and having a draw tube connected with the collection bottle at one end and with the patient at its distal end. The vacuum causes fluids to be drawn from the body cavity into the collection bottle.

The medical vacuum regulator 10 has two modes of operation: continuous and intermittent. However, unlike known regulators, in the electrical medical vacuum regulator 10, the level of regulated vacuum is controlled entirely by electrical signals. In the continuous mode, a level of regulated vacuum within a system regulation chamber 18 is selected by an operator through means of a vacuum selection operator input circuit 24 to continuously apply vacuum through a solenoid controlled pneumatic valve, or solenoid valve, 42 to the patient 14 which is selectively regulated by means including a solenoid valve 20. It should be appreciated that the regulation chamber, or system, 18 is not necessarily distinct from the system tubing 19 shown as connected to an outlet of the regulation chamber 18. In the intermittent mode, as the name suggests, the selected level of regulated vacuum v in the system regulation chamber 18 is intermittently changed on a periodic basis as shown in FIG. 2B. The applied vacuum v has two phases during each period of intermittent operation: a vacuum cycle 21 including a ramp period 29 where the applied vacuum is less than the preselected level, and a maintenance period 31 where the vacuum remains at the preselected level 31 and a relaxation cycle 35 where the patient is relieved to atmospheric pressure. FIG. 2A shows how the vacuum increases with time using a mechanical regulator of the prior art. It is important to note how quickly the vacuum increases with time. FIG. 2B shows how the vacuum increases with time using the electrically controlled regulator of FIG. 1. It should be noted how gradually the vacuum increases with time. Achieving one of the objectives of the invention, during the ramp period 29, the applied regulated vacuum is gradually increased from a first level of preferably one atmosphere, to a selected maximum level, such as V1, FIG. 2B, to avoid the trauma to a patient caused by the vacuum surges created by known regulators. Once the vacuum reaches a maximum vacuum level, V1 for instance, at the end of the ramp period 29, it is maintained at that maximum level for the entire maintenance period 31. At the end of the maintenance period 31, the applied vacuum v is reduced to one atmosphere. Then at the end of the relaxation period 35, the applied vacuum v is again gradually increased to initiate the start of the next cycle.

FIG. 2C illustrates the difference between mechanically controlled regulators of the prior art and the medical regulator 10 of FIG. 1. The curve A is the same curve shown in FIG. 2A. and curve E is the same curve as shown in FIG. 2B. Curve B represents the change in curve A when the bottle is approximately half-full, and curve C represents the change in curve A when the bottle is three-quarters full. Curve E of the invention remains constant regardless of the volume of the bottle. As seen in FIG. 2C, the vacuum surge associated with the mechanical regulator is not only much greater than obtainable with the electrically controlled regulator 10, but the surge gets greater and greater as the bottle fills up with collected fluids. On the other hand, advantageously, the electrically controlled regulator 10 evacuates the bottle at a rate which is constant and independent of the volume of the bottle. The length of time serial 29E is adjustable from as small as the time period 29C to as large as the entire vacuum cycle.

Advantageously, in both modes the electrical medical vacuum regulator 10 is provided with a controller which includes the first solenoid valve, or regulation valve, 20, a comparator 22, a vacuum selection operator input circuit 24, a ramp circuit 26 and a measurement and display circuit 28. The solenoid valve 20 has two states: a de-energized state in which it connects the regulation chamber 18 to atmosphere, or ATM, 30 and an energized state in which the connection to atmosphere 30 is closed.

The comparator 22 determines whether or not the regulation solenoid valve should be energized based on an applied, or actual, vacuum input signal at an input 37 and on a selected vacuum input signal at its input 32. The vacuum input signal at input 37 is obtained from the measurement and display circuit 28 and representative of the vacuum in the vacuum delivery system 16 applied to patient 14. In the intermittent mode, the selected vacuum input signal periodically varies in a way corresponding to the variation of the vacuum shown in FIG. 2B. While in the continuous mode of operation, the selected vacuum input signal is a continuous signal having a selected maximum magnitude corresponding to selected maximum vacuum V1, FIG. 2B.

The comparator circuit 22 compares these two signals at inputs 37 and 32. If the actual vacuum signal exceeds the selected vacuum signal, the solenoid valve 20 is de-energized to allow atmospheric air into the regulation chamber 18 and the remainder of the system to reduce the actual vacuum level delivered to the patient 14. This process continues at a rate dependant on the dynamics of the solenoid valve 20, the point where the vacuum is measured by the measurement and display circuit 28, the volume and restrictions of all the tubing and fittings of the pneumatic system and a relatively small hysteresis for the comparator 22. It should be noted that very fast operation of the solenoid valve on the order of ten to twenty cycles per second is necessary to accomplish a satisfactory regulation of the vacuum in regulation chamber 18. Accordingly, it is preferred to use a solenoid valve with a useful life on the order of fifteen million cycles of operation. While other solenoid valves could be employed, a Series 200 valve made by MAC VALVES, Incorporated of Wixom, Mich. has been found to be satisfactory.

For intermittent operation, a mode selection switch 40 of a mode selection operator input, or mode selection, circuit 36 is actuated to set a memory relay to an intermittent state. An oscillator 34 determines the period of the intermittent signal. In keeping with one aspect of the invention, in the case of power failure, the mode selection switch, or circuit, 36 determines the mode, and thus the state of its output terminals 38 and 40, based on the state of the relay. The mode selection circuit 36 includes means for electronically storing the state of the mode selection switch 36 during a period of power loss and means responsive to the storing means for automatically maintaining the electronic mode selection switch 36 in the one state stored during a period of power loss after the period of power loss has ended. That is, if power is removed, and then restored, the regulator will resume operation in the mode which it was in when it lost power, as will be described in greater detail with reference to FIG. 3.

A mode selection solenoid valve 42 is interposed between the regulation chamber 18 and the patient 14. One output port 44 is connected through a flow rate control orifice 46 to restrict the maximum flow rate to the patient 14 through a patient solenoid positive venting valve 48 when the mode selection circuit 36 is in the intermittent mode. On the other hand, during the continuous mode, the mode selection solenoid valve 42 is energized to connect a second outlet port 50 directly to the vacuum delivery system 16 and patient 14 with no restriction in series with the flow except the inherent restriction of the full diameter of the tubing. Thus, during continuous operation, the patient receives the full flow of vacuum which can be developed in the regulation chamber 18.

Another advantageous feature of the medical vacuum regulator 10 is that power is supplied to mode selection solenoid 42 through one output 38 of the mode selection circuit 36, and power is supplied to the solenoid valve 48 through another output 40. This is done so that, if the regulator 10 is in the intermittent mode and the electronic control fails, the solenoid valve 42 will not be energized, since the mode selection circuit has disconnected it from the controller when the intermittent mode is selected. The patient will not see high flow. When the continuous mode is selected, solenoid valve 48 is energized in a similar manner to prevent the patient 14 from being vented to atmosphere 30 through valve outlet port 35.

In the intermittent mode, the solenoid valve 42 is de-energized to connect the outlet port 44 with the regulation chamber 18 and to close the connection to the outlet port 50. This reroutes the flow through the orifice 46 in order to limit the maximum flow rate of the system. The mode selection circuit 36 also causes the low frequency oscillator 34 to turn on in the intermittent mode. The oscillator determines the cycle duration for both the vacuum cycle 21 and the relaxation cycle 35. During the relaxation cycle 35, solenoid valves 48 and 20 are de-energized. Valve 48 connects atmospheric air to the patient delivery system and shuts off the port connected to line 44. Valve 20 opens the unregulated vacuum source to atmosphere. The command signal applied to input 32 of the comparator 22 is also reduced to zero.

Another object of the invention is achieved by venting the regulation chamber, or system, 18 and thus the unregulated vacuum source 12 during the relaxation cycle 35 to reduce the load on the unregulated vacuum source, or vacuum pump 12. Reducing the load on the vacuum pump 12 increases its useful life and thereby enhanced the reliability of the entire vacuum delivery system. During the relaxation cycle 35, the comparator 22 de-energizes solenoid valve 20 to open to atmosphere 30 and to remain in an open venting position throughout the relaxation cycle 35 to vent the rest of the system. After the relaxation cycle 35, which is selected by means of a control potentiometer 33 associated with the oscillator circuit 34, the system returns to the vacuum cycle 21. In the vacuum cycle 21, which is selected by means of a control potentiometer 33A associated with the oscillator circuit 34, solenoid valve 48 is energized to reapply vacuum through the orifice 46 to the patient 14. The maximum vacuum is selected by means of an operator control potentiometer 23 of the vacuum selection operator input circuit 24. A maximum voltage corresponding to maximum vacuum V1, for instance, is applied to an input 25 of the ramp circuit 26 which first generates a ramp voltage that linearly increases from zero voltage to a preselected maximum voltage corresponding to maximum vacuum V1, FIG. 2B.

Once the ramp output voltage reaches the preselected maximum voltage, it can increase no further, and the maximum voltage is signalled continuously until the end of the vacuum cycle. In the continuous mode, the preselected maximum voltage, for instance, is signalled continuously without interruption. However, in the intermittent mode, the ramp circuit 26 receives a signal at its input 52 from the oscillator 34 which switches off the output of the ramp circuit 26 to a zero voltage and resets the ramp circuit 26 for the next vacuum cycle 21'. The output of the ramp circuit 32 is kept at zero volts by the oscillator 34 until the end of the relaxation cycle 35 and the start of the next vacuum cycle 21', FIG. 2B.

This ramp voltage corresponds to the applied regulated vacuum v, FIG. 2B, and is applied to the comparator input 32 which drives solenoid valve 20. Thus, at the beginning of the cycle, the comparator 22 is regulating to a relatively low level of vacuum compared to the preselected maximum vacuum V1. As time goes on, the ramp voltage, or vacuum command signal, gradually rises and the comparator 22 adjusts for this higher desired vacuum level. This continues until the vacuum command voltage has risen to a maximum value corresponding to the preselected maximum vacuum V1, for instance. For the duration of the vacuum cycle 21, the ramp voltage is maintained at a level corresponding to the maximum vacuum V1. At the end of the vacuum cycle 21 solenoid valve 48 is de-energized to vent the patient 14 to atmosphere 30 and the relaxation cycle 35 of the oscillator 34 repeats, solenoid valve 20 is de-energized to vent the unregulated vacuum source to atmosphere 30.

In the vacuum cycle of the intermittent mode, the percentage of the vacuum cycle dedicated to this slowly rising vacuum ramp 29 is adjustable by means of a potentiometer 27 associated with the ramp circuit 26. The slowly rising ramp period 29 is maintained regardless of the setting on the vacuum level potentiometer 23 and regardless of the volume in the system. As noted above, by gradually applying vacuum, the instant surge of vacuum and flow of known regulators is advantageously eliminated to minimize the occurrence of trauma to the patient 14. The maximum flow rate is also limited by the orifice 46 when in the intermittent mode to further protect the patient against vacuum surge. For instance, if the maximum vacuum level V1 is set to 100 mm Hg, the slowly rising ramp time 29 is set to ten seconds and the duration of the vacuum cycle 21 is thirty seconds, the system will evacuate an empty collection bottle of delivery system 16 from zero to 100 mm Hg in ten seconds. It will then hold that vacuum for twenty more seconds until the beginning of the relaxation cycle 35. If the maximum vacuum level is then changed to 200 mm Hg, for instance, and the bottle volume is reduced from two liters to one liter, the system will evacuate from zero to 200 mm Hg in ten seconds, and will hold that maximum vacuum for twenty more seconds and then begin the relaxation cycle 35.

It should be appreciated that the invention does not reside in the details of assembly for any of the functional blocks. Many circuits are known which can fulfill the requirements of the functional blocks, such as a ramp circuit 26, comparator 22, oscillator 34, vacuum measurement and display circuit 28 and solenoid valves 20, 42, 48 which are well known in the art. Accordingly, no detailed description has been provided therefor. However, referring to FIG. 3, a circuit schematic for a preferred embodiment of the mode selection operator input circuit block 38 is shown.

Referring to FIG. 3, the mode selection operator input block 36, has two normally open, momentary contact: push button switches 62 and 68 which are provided for selective manual energization of a set coil 70 and a reset coil 72 respectively connected in parallel with each other between a pair of DC supply voltage terminals +VS1 and −VS1, preferably 12 V DC. When the set coil 70 is energized, the switch 58 is moved to the position 60 as shown to energize solenoid 48 and de-energize solenoid valve 42. When the reset coil 72 is energized, the switch 58 is moved to the position 66 to de-energize solenoid 48 and to energize solenoid valve 42. Another switch 54 switches to a position 56 when switch 58 is switched to position 60, as shown, and switched to a position 64 when switch 58 is in position 66. When in position 56, a flip-flop 74 switches output 40 connected to the oscillator 34, FIG. 1, to a logic one state to cause the oscillator 34 to operate for the intermittent mode. Otherwise, when in position 64, the flip-flop 74 is in a logic zero state to cause the regulator to operate in the continuous mode. Accidental high flow is unlikely since both the flip-flop and the relay switch 58 must be in the requisite states for this to occur.

Advantageously, positions 64 and 66 have permanent magnets 64' and 66' respectively associated therewith for holding the contacts in those positions once selected by the electronic or temporary contact switches 62 and 68 in the event of a loss of AC power. In this way, when power is returned, the mode of operation after power failure will be the same mode of operation selected prior to power failure.

While a particular embodiment has been described in detail, it should be appreciated that many variations may be made thereto without departing from the scope of the invention as defined in the appended claims. For instance, while a linear ramp circuit has been employed, the gradually increasing vacuum need not be linear in order to obtain the surge protection obtained by the invention. While the regulator has been disclosed with reference to a medical application, it should be appreciated that it could also be used in other applications such as in hospitals, industrial plants and pharmaceutical plants to control vacuum or pressure levels. Also, while the regulator valve has been shown as controlled by electrical signals, it is also contemplated that the control signals could be photo signals, magnetic signals, pneumatic, hydraulic or other control signals from a suitable control signal source, in which case the block diagram of FIG. 1 would remain substantially the same while only the nature of the signals would change.

I claim:

1. In a medical vacuum regulator for applying regulated vacuum to a patient delivery system from an unregulated vacuum source connectable with the regulator, the improvement being a controller, comprising:
    means for electromechanically regulating vacuum applied to the patient delivery system to provide a preselected level of vacuum; and
    means connected to the electromechanically regulating means for electrically controlling the regulating means to vary the preselected level of vacuum applied to the patient, including
        means for intermittently decreasing the preselected level of vacuum, and
        means for automatically, intermittently increasing the preselected level of vacuum to a preselected maximum level gradually to reduce vacuum surge trauma.

2. The medical vacuum regulator of claim 1 in which said controlling means includes means for maintaining the applied vacuum at a preselected level after the applied vacuum is increased to the preselected level by said gradually increasing means.

3. The medical vacuum regulator of claim 2 in which said gradually increasing means includes
   means for generating a ramp, and
   means responsive to the ramp for gradually increasing the applied vacuum on a linear basis from a first level to the preselected maximum level.

4. The medical vacuum regulator of claim 3 including switching means for establishing a preselected period of a vacuum cycle for gradually increasing the vacuum from the first level to the preselected maximum level.

5. The medical vacuum regulator of claim 4 including means for selectively varying the preselected vacuum cycle period.

6. The medical vacuum regulator of claim 1 in which said intermittently decreasing means decreases the applied vacuum at a rate substantially greater than the rate at which said gradually increasing means gradually increases the vacuum.

7. The medical vacuum regulator of claim 1 in which said gradually increasing means includes means for gradually increasing applied vacuum to the preselected maximum level on a linear basis.

8. In a medical vacuum regulator for supplying a regulated vacuum to a patient delivery system from an unregulated, substantially continuous vacuum source connectable with the regulator, the improvement being a controller, comprising:
   means for continuously venting the patient delivery system to atmosphere during periodic patient venting periods;
   means for automatically venting the unregulated vacuum source to atmosphere during the periodic patient venting periods to reduce the load on said unregulated vacuum source when connected with the regulator; and
   means electrically connected to the patient delivery system venting means and to the vacuum source venting means for controlling the unregulated source venting means to alternately vent and not vent the unregulated, vacuum source during vacuum periods occurring between the periodic patient venting periods to achieve regulation at preselected vacuum levels during the vacuum periods.

9. The vacuum regulator claim 8 including means for controlling said venting means to simultaneously and continuously vent both the patient and the source of vacuum throughout the period of patient venting.

10. The vacuum regulator of claim 9 including means for selectively changing the duration of the patient venting period.

11. The vacuum regulator of claim 8 in which said means for venting the patient is a solenoid valve.

12. The vacuum regulator of claim 8 in which said means of venting the source of vacuum is a solenoid valve.

13. The vacuum regulator of claim 12 including means for causing said solenoid valve to open and close at a rate on the order of twenty cycles per second to regulate the vacuum when not continuously venting.

14. In an electrically powered medical vacuum regulator with continuous and intermittent modes of operation in which vacuum is continuously and intermittently applied to a patient, respectively, the improvement being a mode control circuit, comprising:
   means including an electronic mode selection switch manually actuatable for alternatively selecting said continuous mode and said intermittent mode, respectively; and
   means responsive to the electronic mode selection switch for selectively establishing operation in said continuous and intermittent modes including storing the last selection of mode selection switch during a period of power loss to the regulator.

15. The electrically powered medical vacuum regulator of claim 14 in which
   said selectively establishing operation means includes a drive switch, and
   said storing means includes means for nonelectronically latching the drive switch into the last position it is placed in response to an actuation of the electronic mode selection switch.

16. The electrically powered medical vacuum of claim 14 in which said latching means includes a permanent magnet.

17. The electrically powered medical vacuum regulator of claim 14 including a means for automatically venting the patient during said period of power loss to the regulator.

18. A regulator, comprising:
   regulation chamber connectable to an unregulated source of vacuum;
   a regulating venting electromechanically operable valve to selectively vent the regulation chamber;
   means for preselecting a regulated vacuum level; and
   means electrically connected to both the regulating venting valve and the preselecting means and responsive to said preselecting means for generating signals to control the regulating valve to alternately open to vent and close a plurality of times per second to directly achieve regulation in the regulation chamber at said preselected regulated vacuum level.

19. The regulator of claim 18 in which the control means includes
   a sensor for generating a sensor signal representative of an actual vacuum being regulated, and
   means responsive to the sensor signal to control the venting valve.

20. The regulator of claim 19 in which the sensor signal responsive control means includes
   a comparator responsive to the sensor, and
   means responsive to the comparator to control the venting valve.

21. The regulator of claim 18 in which the signals are electrical signals.

22. In a medical vacuum regulator for applying regulated vacuum to a patient delivery system, the improvement being a controller, comprising:
   a regulation chamber connected with a regulating valve, the regulating valve having means for automatically, alternately opening and closing to change the: regulated vacuum; and
   means to control the regulating valve to gradually change the regulated vacuum to a preselected level by alternately opening and closing a plurality of times per second.

* * * * *